(12) United States Patent
Trznadel et al.

(10) Patent No.: US 10,159,824 B2
(45) Date of Patent: Dec. 25, 2018

(54) MULTI-CHAMBER CONTAINER APPARATUSES AND METHODS OF MAKING AND USING THE SAME

(71) Applicant: Joseph Trznadel, Crystal Lake, IL (US)

(72) Inventors: Joseph Trznadel, Crystal Lake, IL (US); Mychal Trznadel, Crystal Lake, IL (US); Conner Trznadel, Crystal Lake, IL (US)

( * ) Notice: Subject to any disclaimer, the term of this patent is extended or adjusted under 35 U.S.C. 154(b) by 379 days.

(21) Appl. No.: 15/162,731

(22) Filed: May 24, 2016

(65) Prior Publication Data

US 2017/0341846 A1 Nov. 30, 2017

(51) Int. Cl.
*B65D 69/00* (2006.01)
*A61M 35/00* (2006.01)
*A61F 13/40* (2006.01)
*A45D 34/04* (2006.01)
*A46B 9/02* (2006.01)

(52) U.S. Cl.
CPC ......... *A61M 35/006* (2013.01); *A45D 34/042* (2013.01); *A45D 34/045* (2013.01); *A46B 9/028* (2013.01)

(58) Field of Classification Search
CPC . A61M 35/006; A45D 34/042; A45D 34/045; A45D 40/0087; A46B 9/028; A46D 1/0207
USPC ..... 206/15.2, 15.3, 209, 210, 229, 361, 362; 604/1–3; 132/200, 218; 401/129
See application file for complete search history.

(56) References Cited

U.S. PATENT DOCUMENTS

| | | | | |
|---|---|---|---|---|
| 4,206,843 A | * | 6/1980 | Rainey | A61B 18/06 206/210 |
| 4,211,323 A | * | 7/1980 | Olsen | A61B 10/0096 206/210 |
| 4,600,328 A | * | 7/1986 | Clements | A45D 40/24 132/218 |
| 4,952,204 A | * | 8/1990 | Korteweg | A61M 35/006 206/363 |
| 5,052,839 A | * | 10/1991 | Pettengill | A45D 40/265 401/10 |
| 5,112,152 A | * | 5/1992 | McBride | A45D 40/0087 206/209 |
| 6,406,451 B1 | | 6/2002 | Rowe | |
| 6,516,947 B1 | * | 2/2003 | Van Dyke | A45D 34/042 206/361 |
| 6,957,958 B2 | | 10/2005 | Rowe et al. | |
| 7,476,046 B2 | | 1/2009 | Phillips et al. | |
| 8,100,294 B2 | | 1/2012 | May et al. | |

(Continued)

*Primary Examiner* — Luan K Bui
(74) *Attorney, Agent, or Firm* — Scherrer Patent & Trademark Law, P.C.; Stephan T. Scherrer; Monique A. Morneault

(57) ABSTRACT

The present invention relates to multi-chamber containers. Specifically, the multi-chamber containers comprise, generally, a first container having a swab or applicator contained therein and a second container having a solution therein. In various embodiments, a first container may comprise a fracture recess for breaking and removing the swab or applicator, and a second container may further comprise a fracture recess for opening and exposing the solution. In embodiments, first and second containers are disposed separately, or connectedly side-by-side. In embodiments, a second container is contained within a first container.

15 Claims, 10 Drawing Sheets

(56) References Cited

U.S. PATENT DOCUMENTS

| | | | |
|---|---|---|---|
| 8,181,777 B2 | 5/2012 | Suchan et al. | |
| 8,216,171 B2 * | 7/2012 | Kamen | A61M 35/006 |
| | | | 604/1 |
| 8,434,643 B2 | 5/2013 | Harris et al. | |
| 8,585,308 B2 | 11/2013 | May | |
| 8,631,941 B2 | 1/2014 | Fazzolari | |
| 8,740,831 B2 | 6/2014 | Wu | |
| 8,910,830 B2 | 12/2014 | May | |
| 2003/0233063 A1 * | 12/2003 | Nakatani | A61F 13/38 |
| | | | 604/2 |
| 2006/0095000 A1 | 5/2006 | Kimmell | |
| 2011/0248045 A1 | 10/2011 | Harris et al. | |

\* cited by examiner

MULTI-CHAMBER CONTAINER APPARATUSES AND METHODS OF MAKING AND USING THE SAME

TECHNICAL FIELD

The present invention relates to multi-chamber container apparatuses. Specifically, the multi-chamber container apparatuses comprise, generally, a first container having a swab or applicator contained therein and a second container having a solution therein. In various embodiments, a first container may comprise a fracture recess for breaking and removing the swab or applicator, and a second container may further comprise a fracture recess for opening and exposing the solution. In embodiments, first and second containers are disposed separately, or connectedly side-by-side. In embodiments, a second container is contained within a first container.

BACKGROUND

Containers for holding solutions are, of course, generally known. Indeed, jars containing medicines, solutions or other like fluids, for example, go back hundreds of years to the earliest uses of ceramic materials. Upon the introduction of glass, glass vials or ampoules were developed to be usefully suited to hold sterile solutions and/or medicines. Indeed, the first glass ampoule for storing sterile solutions was developed by a French pharmacist, Stanislaus Limousin, in 1890. This vial had a main body and a long tapered neck that was sealed after solutions were placed in the maid body. The neck could then be broken and the solution extracted.

Glass is still used to this day for vials and ampoules, as the material is useful for holding solutions. However, because glass has a tendency to shatter upon breaking, there is a risk of getting glass shards within the solution if not broken and opened properly. While new types of glass materials have been developed to minimize the shattering thereof, other materials have been found to also be useful for use in holding sterile solutions, namely, thermoplastics. Indeed, thermoplastics are useful because they can be shaped and manipulated relatively easily into vials, ampoules and other like containers. Further, thermoplastics tend not to shatter like glass, preventing the imposition of the solutions with glass shards that may be damaging to a user. However, unlike glass, thermoplastics can be relatively difficult to break, as the polymer chain entanglement of the thermoplastics provides a certain degree of toughness and resiliency to the walls of containers made therefrom.

Therefore, thermoplastic vials or ampoules have been known to have points of weakness built in to the structures themselves, allowing vials and ampoules to be opened at specific locations when desired. Specifically, U.S. Pat. No. 6,516,947 to Van Dyke et al., for example, discloses a plastic container having a main body portion and a long tapered neck portion, and a fracture recess on the body thereof that is an area of reduced thickness, allowing a user to squeeze or bend the vial at this region, causing the main body portion to break.

It is also generally known to provide containers having swab applicators therein. Swab applicators typically include a swab having an applicator head connected to a handle. The swab is contained within a closed container package which can be opened to expose the swab for use. The swab may be coated or soaked in a medical fluid, for example, which can then be applied to a patient, such as on a wound.

One example of a swab applicator can be found in U.S. Pat. No. 4,952,204 to Korteweg, which describes a swab contained within a sleeve which can be opened by use of manual force. The swab has a substance which can be applied by the swab. The swab has a straight hollow plastic stick with a bud of cotton attached on one end. The sleeve consists of a relatively small diameter cylindrical handle portion at one end, a substantially larger diameter receptacle portion at the opposite end, and a transition portion of compound configured therebetween. A tip of the handle portion of the sleeve engages a tip of the swab stick. The intersection between the receptacle and transition portions forms a sharp angle on an interior of the sleeve. The sleeve is opened by squeezing the sleeve at the intersection between the receptacle and transition portions and breaking the sleeve at the interior sharp angle.

Examples of other containers include applicators or dispensers having sharp interior angles to open the containers, and include U.S. Pat. Nos. 4,927,012, 5,220,061, and 5,326,603. The aforementioned Van Dyke et al. patent, U.S. Pat. No. 6,516,947 discloses a swab applicator extending within a sleeve portion of the container, whereupon breakage of the main body at a fracture recess, the swab applicator, preferably having a solution thereon, may be extracted from the container. Thus, the sleeve maintains its position around the swab applicator handle, thereby minimizing contamination.

However, before now, it has been difficult to provide an applicator apparatus where two or more solutions may be maintained separately to ensure that they do not mix until necessary. For example, oftentimes two or more solutions may be reactive with each other, and it may be preferred to utilize the solutions immediately upon mixing to maximize their use. In another example, a mixture of two solutions may have a limited shelf-life, and thus component solutions may be desired to be kept separate to maximize their longevity. Moreover, merely the presence of the swab applicator in a single solution may be enough to cause degradation of the solution and/or the swab applicator. A need, therefore, exists for multi-chamber container apparatuses and methods of making and using the same. Specifically, a need exists for multi-chamber container apparatuses and methods of making and using the same that maintains separation of two or more solutions until desired. In addition, a need exists for multi-chamber container apparatuses and methods of making and using the same that maintains separation of a swab applicator and one or more solutions to prevent degradation of the one or more solutions and/or the swab applicator apparatus.

Systems for maintaining separation of solutions, however, are generally known. Indeed, it is known to provide ampoules having internal tubes or chambers that may be broken internally for solutions to mix prior to application thereof. However, many of these solutions utilize internal chambers made of glass, and generally do not solve the problems with potential glass shards and/or fine glass particulates ending up in the mixed solution. Further solutions utilizing internal thermoplastic chambers have not solved the problems associated with maintaining applicators in sterile environments until use before, during and/or after application of the solution thereon. A need, therefore, exists for multi-chamber container apparatuses having internal chambers that may easily be broken to allow application of solution to a swab applicator. Moreover, a need exists for multi-chamber container apparatuses having internal chambers that may be broken to allow mixing of separate solutions prior to or during application to a swab applicator.

While it may be known to mix solutions within containers, it is often difficult to determine when mixing is sufficient prior to use. For example, if solutions are not properly mixed prior to application, especially for medical use, the resultant solution may be ineffective for its intended purpose. A need, therefore, exists for multi-chamber container apparatuses and methods of making and using the same that allow a user to know when solutions are sufficiently mixed. More specifically, a need exists for multi-chamber container apparatuses and methods of making and using the same that provide a visual indicator of sufficient mixing.

SUMMARY OF THE INVENTION

The present invention relates to multi-chamber containers. Specifically, the multi-chamber containers comprise, generally, a first container having a swab or applicator contained therein and a second container having a solution therein. In various embodiments, a first container may comprise a fracture recess for breaking and removing the swab or applicator, and a second container may further comprise a fracture recess for opening and exposing the solution. In embodiments, first and second containers are disposed separately, or connectedly side-by-side. In embodiments, a second container is contained within a first container.

To this end, in an embodiment of the present invention, a multi-chamber container apparatus is provided. The multi-chamber container comprises: a first chamber having a main body portion and an extended portion, the first chamber having a wall and an area of weakness within the wall for separating the main body portion and the extended portion from each when the first chamber is broken at the area of weakness, and an applicator disposed within the first chamber having a handle and an applicator end, the handle of the applicator extending from the extended portion such that the applicator end is disposed within the main body portion; a second chamber having a main body portion and an extended portion, the second chamber having a wall and an area of weakness within the wall for separating the main body portion and the extended portion of the second chamber from each other when the second chamber is broken at the area of weakness, and a first material within the second chamber for application to the applicator end when the applicator end is inserted into the second chamber, wherein the first and second chamber are connected to each other in a side-by-side configuration.

In an embodiment, the applicator end is a swab.

In an embodiment, the first material is selected from the group consisting of a liquid, a powder and a gel.

In an embodiment, the multi-chamber container apparatus further comprises: a fin disposed between the first and second chambers for separating the first and second chambers from each other.

In an embodiment, the wall of the first chamber and the wall of the second chamber are interconnected together.

In an embodiment, the multi-chamber container further comprises a transitional neck between the main body portion and the extended portion of the first chamber.

In an embodiment, the area of weakness is disposed on the transitional neck.

In an embodiment, the multi-chamber container apparatus further comprises a second material contained within the second chamber, wherein the second material is selected from the group consisting of a liquid, a powder and a gel.

In an embodiment, the multi-chamber container apparatus further comprises a capsule within the first or second chambers, wherein the capsule comprises an area of weakness for opening the capsule, the capsule further comprising a second material wherein the second material is selected from the group consisting of a liquid, a powder and a gel.

In an embodiment, the capsule is in the second chamber, such that breaking the capsule at the area of weakness causes the first and second materials to mix.

In an alternate embodiment of the present invention, a method of using a multi-chamber container apparatus is provided. The method comprises the steps of: providing a multi-chamber container apparatus comprising a first chamber having a main body portion and an extended portion, the first chamber having a wall and an area of weakness within the wall for separating the main body portion and the extended portion from each when the first chamber is broken at the area of weakness, and an applicator disposed within the first chamber having a handle and an applicator end, the handle of the applicator extending from the extended portion such that the applicator end is disposed within the main body portion; a second chamber having a main body portion and an extended portion, the second chamber having a wall and an area of weakness within the wall for separating the main body portion and the extended portion of the second chamber from each other when the second chamber is broken at the area of weakness, and a first material within the second chamber for application to the applicator end when the applicator end is inserted into the second chamber, wherein the first and second chamber are connected to each other in a side-by-side configuration; breaking the first chamber at the area of weakness on the first chamber; breaking the second chamber at the area of weakness on the second chamber; withdrawing the applicator from the first chamber; and inserting the applicator into the second chamber and applying the first material to the applicator.

In an embodiment, the applicator end is a swab, and the first material is absorbed by the swab when inserted into the second chamber.

In an embodiment, the second chamber comprises a second material and the method further comprises the step of mixing the first and second materials together when the applicator is inserted into the second chamber.

In an embodiment, the first or second chambers comprise a capsule within the first or second chambers, wherein the capsule comprises an area of weakness for opening the capsule, the capsule further comprising a second material, and further the method comprises the step of breaking the capsule at the area of weakness and releasing the second material into the first or second chamber.

In an embodiment, the capsule is in the second chamber, such that breaking the capsule at the area of weakness causes the first and second materials to mix to form a mixture, and the method further comprises the step of applying the mixture to the applicator when the applicator is inserted into the second chamber.

In an alternate embodiment of the present invention, a multi-chamber container apparatus is provided. The multi-chamber container comprises a first chamber having a main body portion and an extended portion, the first chamber having a wall and an area of weakness within the wall for separating the main body portion and the extended portion from each when the first chamber is broken at the area of weakness, and an applicator disposed within the first chamber having a handle and an applicator end, the handle of the applicator extending from the extended portion such that the applicator end is disposed within the main body portion; and a second chamber within the first chamber, the second chamber comprising a wall, an interior space and an area of weakness, the second chamber further comprising a first material.

In an embodiment, breaking the area of weakness on the second chamber causes the first material to be released into the first chamber and onto the applicator.

In an embodiment, the multi-chamber container apparatus further comprises a second material within the first chamber, wherein when the first material is released into the main body portion, the first material and the second material mix to form a mixture.

In an embodiment, the mixture comprises a color indicating that the first and second materials have properly mixed.

In an embodiment, the applicator is disposed within both the first chamber and the second chamber at the same time until removed by breaking of the areas of weakness on both the first and second chambers.

It is, therefore, an advantage and objective of the present invention to provide multi-chamber container apparatuses and methods of making and using the same.

Specifically, it is an advantage and objective of the present invention to provide multi-chamber container apparatuses and methods of making and using the same that maintains separation of two or more solutions until desired.

In addition, it is an advantage and objective of the present invention to provide multi-chamber container apparatuses and methods of making and using the same that maintains separation of a swab applicator and one or more solutions to prevent degradation of the one or more solutions and/or the swab applicator apparatus.

Moreover, it is an advantage and objective of the present invention to provide multi-chamber container apparatuses having internal chambers that may be broken to allow application of solution to a swab applicator.

Further, it is an advantage and objective of the present invention to provide multi-chamber container apparatuses having internal chambers that may be broken to allow mixing of separate solutions prior to or during application to a swab applicator.

In addition, it is an advantage and objective of the present invention to provide multi-chamber container apparatuses and methods of making and using the same that allow a user to know when solutions are sufficiently mixed.

More specifically, it is an advantage and objective of the present invention to provide multi-chamber container apparatuses and methods of making and using the same that provide a visual indicator of sufficient mixing.

Additional features and advantages of the present invention are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE PRESENTLY PREFERRED EMBODIMENTS

The present invention relates to multi-chamber containers. Specifically, the multi-chamber containers comprise, generally, a first container having a swab or applicator contained therein and a second container having a material, such as a liquid, powder or gel therein. In various embodiments, a first container may comprise a fracture recess for breaking and removing the swab or applicator, and a second container may further comprise a fracture recess for opening and exposing the solution. In embodiments, first and second containers are disposed separately, or connectedly side-by-side. In embodiments, a second container is contained within a first container.

Figure 1:
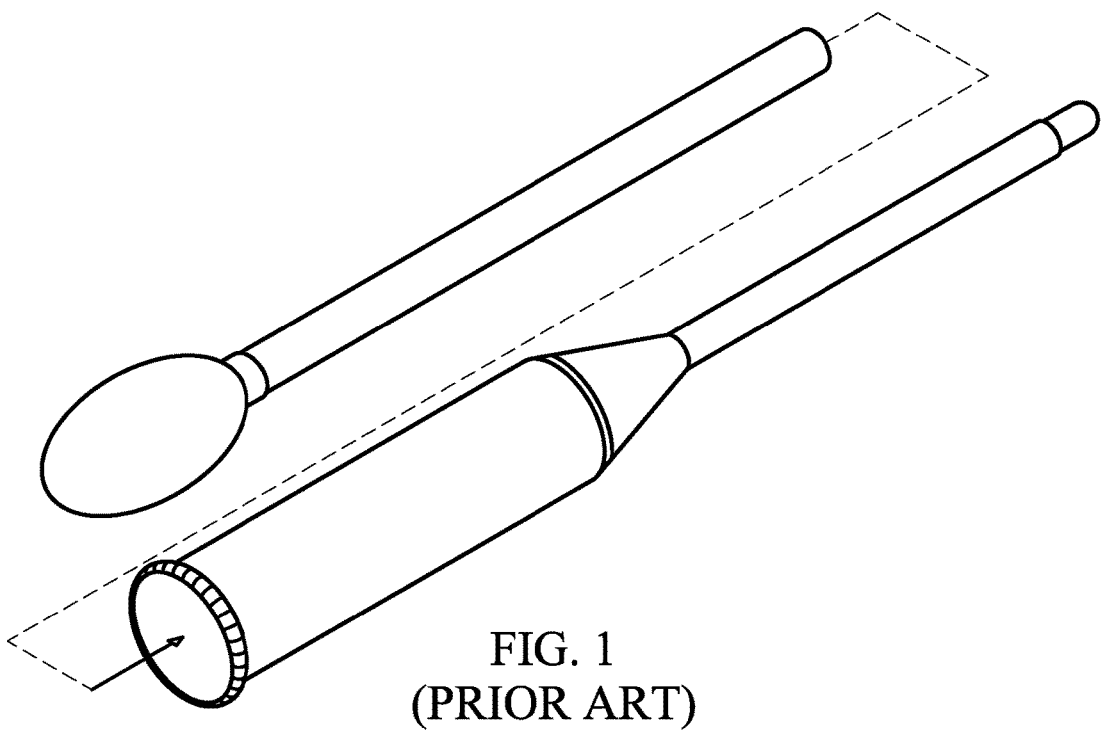
FIG. 1 illustrates a perspective view of a prior art container having a swab contained therein.
Figure 2:
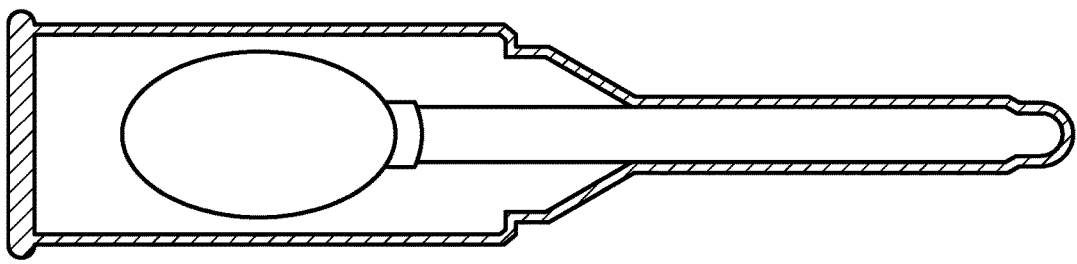
FIG. 2 illustrates a cross-sectional view of a prior art container having a swab contained therein.

FIGS. 1 and 2 illustrate a prior art container apparatus, wherein a swab is disposed within the container apparatus. As described in prior art, the container apparatus may be broken on a line or an area of weakness in one or a plurality of locations to remove the swab from within the container apparatus. A material, such as a liquid, powder or gel may be contained within the prior art container apparatus for contacting the swab such that the material may be removed from the container and utilized on the swab. As stated herein, the term "material" may be synonymous with solution, liquid, powder or gel when used throughout the present specification.

Figure 3:
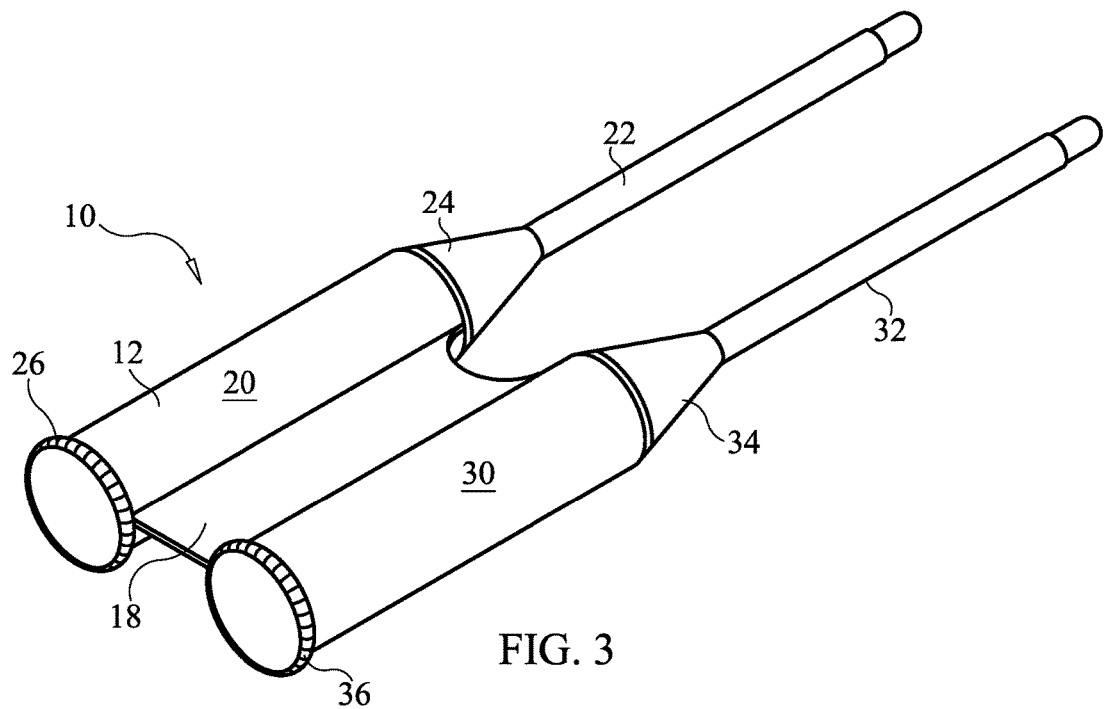
FIG. 3 illustrates a perspective view of a multi-chamber container apparatus in an embodiment of the present invention.

Now referring to the figures, wherein like numerals refer to like parts, FIG. 3 illustrates a multi-chamber container apparatus 10 in an embodiment of the present invention. Specifically, the multi-chamber container apparatus 10 comprises a first chamber 12 and a second chamber 14 disposed in side-by-side relation to each other. The first chamber 12 comprises a main body portion 20, a stem portion 22 and a transitional neck portion 24. Likewise, the second chamber 14 comprises a main body portion 30, a stem portion 32 and a transitional neck portion 34. A connecting fin 18 may bridge the first chamber 12 and the second chamber 14 so as to maintain the multi-chamber apparatus 10 as a singular unit.

Disposed on an end of each of the first and second chambers 12, 14 may be closed off areas 26, 36, respectively, that may be sealed after materials, such as solutions and/or swabs, are added to the first and second chambers, 12, 14. For example, main body portions 20, 30 may each have an open end (not shown) prior to filling thereof. Once filled with material, the open end may be pinched shut and heat-sealed forming closed off areas 26, 36.

It should be noted that the first and second chambers 12, 14 may be connected to each other in any manner. For example, the connecting fin 18 may allow the first and second chambers 12, 14 a distance apart from each other so that each chamber can maintain its own physical integrity, as placing immediately side-by-side may cause points of weakness in the sidewalls of one or the other of the first and second chambers 12, 14. Alternatively, the first and second chambers 12, 14 may be disposed immediately adjacent each other without connecting fin 18 without consequent weakening of side walls, and the present invention should not be limited as described herein. Moreover, although the present embodiments disclose multi-chamber container apparatuses having, generally, two chambers, it should be noted that the multi-chamber apparatus 10 may comprise more than two chambers, as necessary for any particular application.

Figure 4:
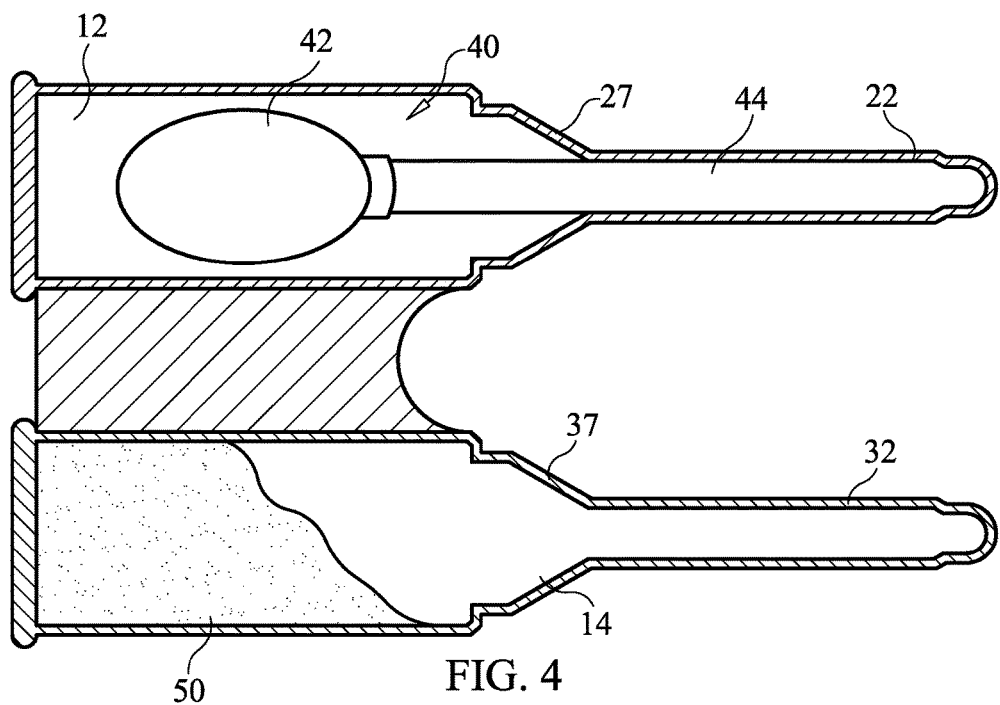
FIG. 4 illustrates a cross-sectional view of a multi-chamber container apparatus in an embodiment of the present invention.

FIG. 4 illustrates a cross-sectional view of multi-chamber container apparatus 10 in an embodiment of the present invention. The multi-chamber container apparatus 10 may preferably be made from a thermoplastic material, such as, for example, polyethylene or polypropylene, although the multi-chamber container apparatus 10 may be made from any other material sufficient to perform as described herein, and the present invention should not be limited as described herein. Moreover, the first and second chambers 12, 14 may be made of a material that is any color, and may be opaque, transparent, or translucent. In a preferred embodiment, the first and second chambers 12, 14 may be transparent or translucent so that a user may view the contents therein. Alternatively, the first and second chambers 12, 14 may be made from a combination of materials, some of which may be opaque, and some of which may be transparent or translucent so as to provide a window for a user to see therein.

As shown in FIG. 4, first chamber 12 may contain a swab or applicator 40 having an applicator end 42 and a handle 44 extending therefrom. The applicator end 42 may be any material that may be used to apply a solution as needed. For example, the applicator end 42 may be a cotton swab that may absorb a medicament that may be applied to a wound. Of course, the applicator end 42 may be any shape and/or made from any material, and the present invention should not be limited as disclosed herein.

The handle 44 may extend from the applicator end 42 and may be disposed within the stem 22 of the first chamber 12. Thus, a user may grasp the stem 22 and utilize the applicator end 42 without touching the handle 44, thereby minimizing or eliminating contamination of the applicator end 42. Alternatively, the stem 22 and the handle 44 may be a unitary piece instead of separate pieces as described herein.

The second chamber 14 may preferably have a solution 50 disposed therein. The solution 50 may be any solution needed by a user thereof for a specific purpose. Preferably, the solution may be a medicament or salve that may be utilized for a medical purpose, for cleaning a wound, applying medicine, or for any other purpose. Alternatively, the second chamber 14 may have a dry material therein, such as a dry powder, that may adhere to and be extracted by the swab or applicator 40, as described herein.

Figure 5:
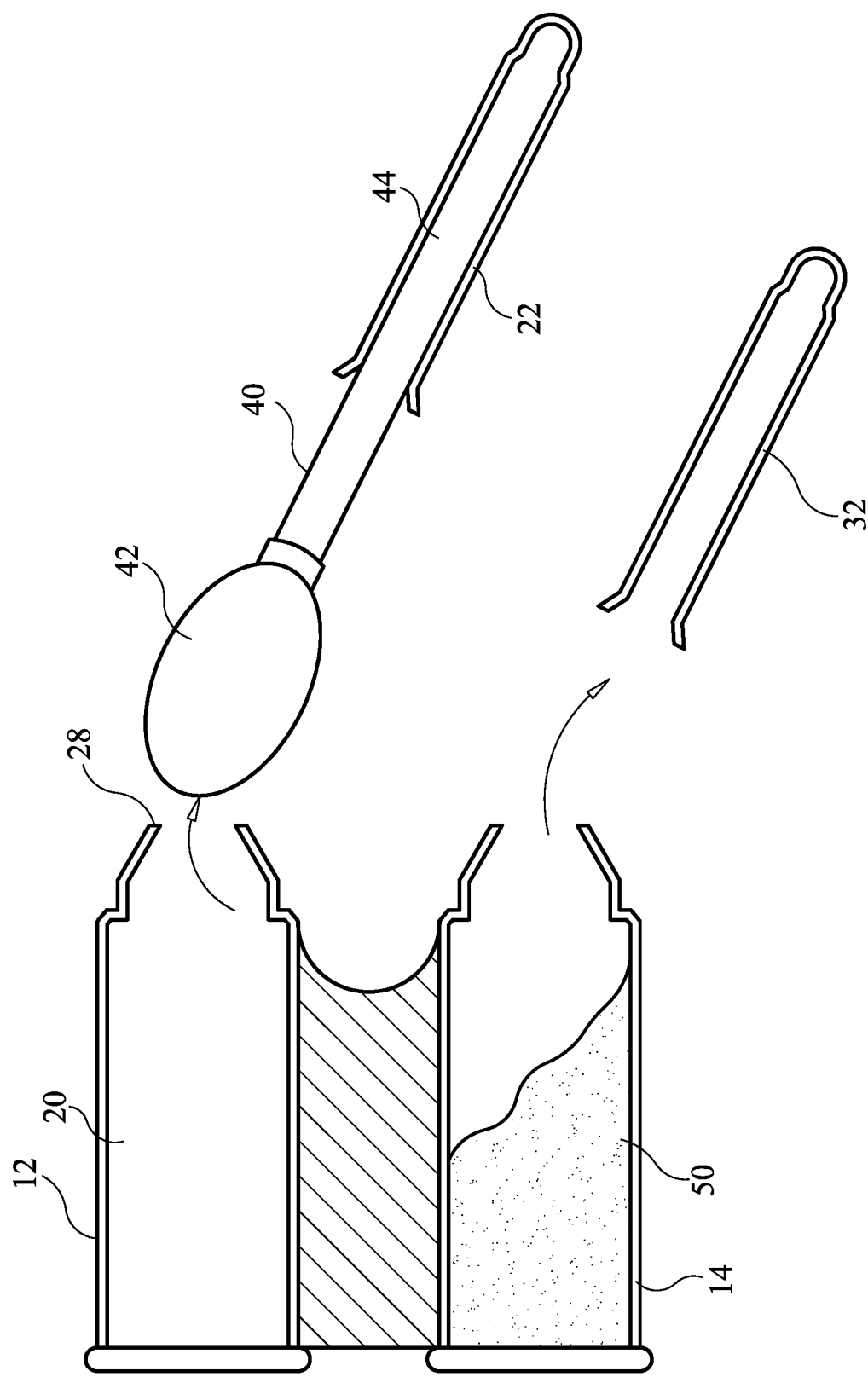
FIG. 5 illustrates a cross-sectional view of a multi-chamber container apparatus having caps and a swab removed in an embodiment of the present invention.
Figure 6:
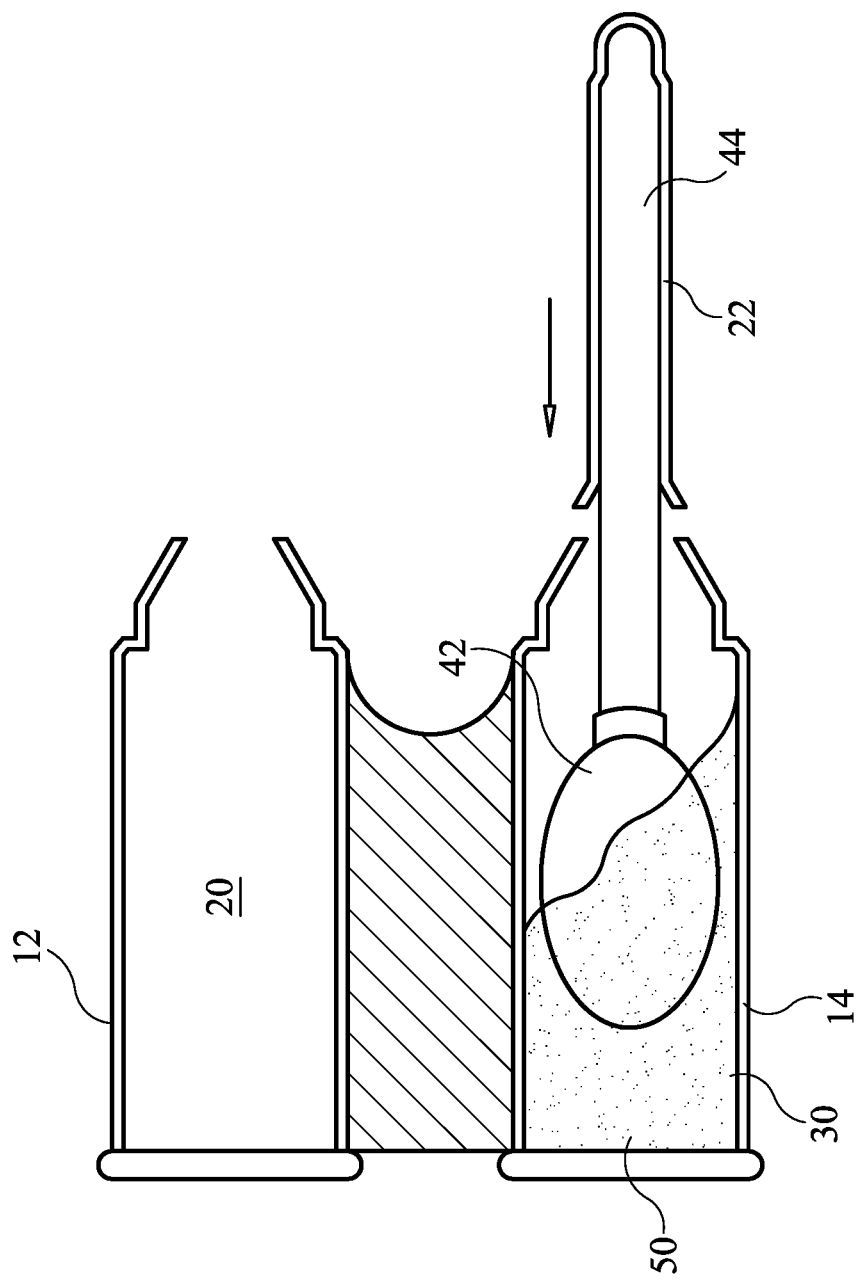
FIG. 6 illustrates a cross-sectional view of a multi-chamber container apparatus having a swab from a first chamber inserted into a second chamber in an embodiment of the present invention.
Figure 7:
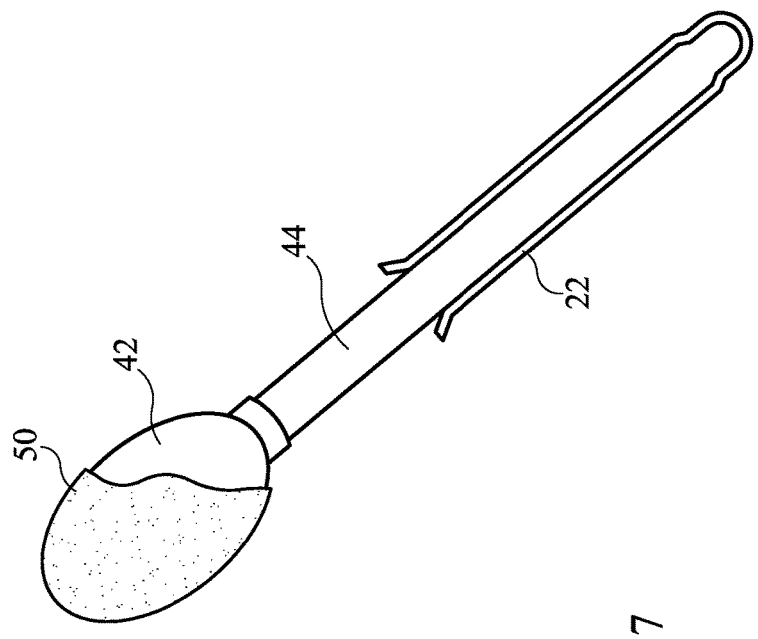
FIG. 7 illustrates a cross-sectional view of a multi-chamber container apparatus having a swab removed from a second chamber in an embodiment of the present invention.
Figure 7:
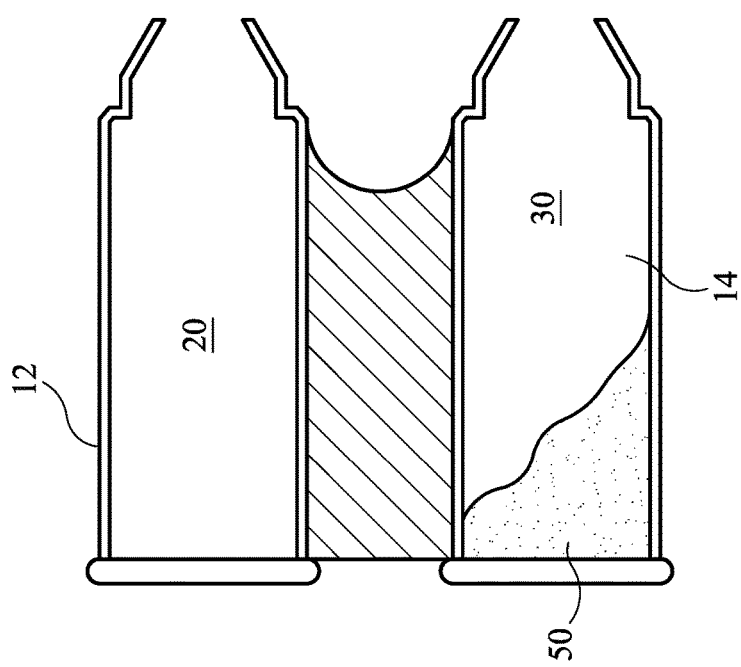

As illustrated in FIGS. 5, 6 and 7, a method of using the multi-chamber container apparatus is shown. Specifically, FIG. 5 illustrates that the stems 22, 32 may be removed from the first and second chambers 12, 14, respectively. This may be done by grasping the stems 22, 32 and breaking the stems 22, 32 from the main body portions 20, 30, respectively. Specifically, the first and second chambers 12, 14 may each have a line or area of weakness 27, 37, respectively, strategically placed on each of the first and second chambers 12, 14, such that the walls of each chamber may be broken when grasped and pulled, squeezed, or otherwise manually manipulated. As illustrated in FIG. 5, the lines or areas of weakness may be on or near the transitional neck portions 24, 34 of the first and second chambers 12, 14, respectively. However, it should be noted that the lines or areas of weakness may be located anywhere on the first and second chambers 12, 14, such as on the stems 22, 32, on the neck portions 24, 34, and/or on the main body portions 20, 30.

The lines or areas of weakness, also known as "fracture recesses" may be portions of the first and second chambers 12, 14 where the thickness of the walls thereof may be weakened via a score line, or may be thinner than in the rest of the first and second chambers 12, 14. The lines or areas of weakness may be molded thereinto or scored after molding the same, or placed or disposed in the walls of the first and second chambers 12, 14 in any manner. Specifically, the lines or areas of weakness may extend from an exterior surface of the walls of the first and second chambers 12, 14 into the walls thereof. Thus, the walls may have reduced wall thickness at the fracture recesses. The fracture recesses may have various shapes, such as V-shape, U-shape, or any other shape, and should not be limited as described herein.

As illustrated in FIG. 5, the stem 22 containing the handle 44 of the swab or applicator 40 may be broken away from the main body portion 20 of the first chamber 12 at a first fracture recess forming a first break point 28, thereby removing the swab or applicator 40 from the first chamber 12. Likewise, the stem 32 of the second chamber 14 may be grasped, broken and removed from the main body portion 30 of the second chamber 14 at a second fracture recess forming a second break point 38, thereby exposing the solution 50 contained therein.

As illustrated in FIG. 6, the applicator 40 may then be inserted into the main body portion 30 of the second chamber, thereby causing the solution 50 to contact the applicator end 42 of the applicator 40, allowing the solution 50 to be absorbed in, adhered on, or otherwise associated with the applicator end 42. A user may then bring the applicator end 42 and, thus, the solution 50 out of the second chamber, as shown in FIG. 7, and the user may thus utilize the solution 50 as needed. Preferably, the applicator end 42 is made from an absorbent material, and the solution 50 may be absorbed by the applicator end 42 and readily dispensed as necessary.

In another embodiment of the present invention, the first chamber 12 may contain a stirring stick as the applicator 40 extending from the stem 22, and the applicator end 42 may be a paddle or other surface that may be utilized for stirring a drink. The solution 50 may be an edible additive that may be added to the drink. The edible additive may be poured from the second chamber 14 and the stirring stick may be utilized to stir the drink. For example, the solution 50 may be a creamer, and may be added to hot coffee, and the stirring stick may be utilized to stir the creamer in the coffee when added thereto.

Figure 8:
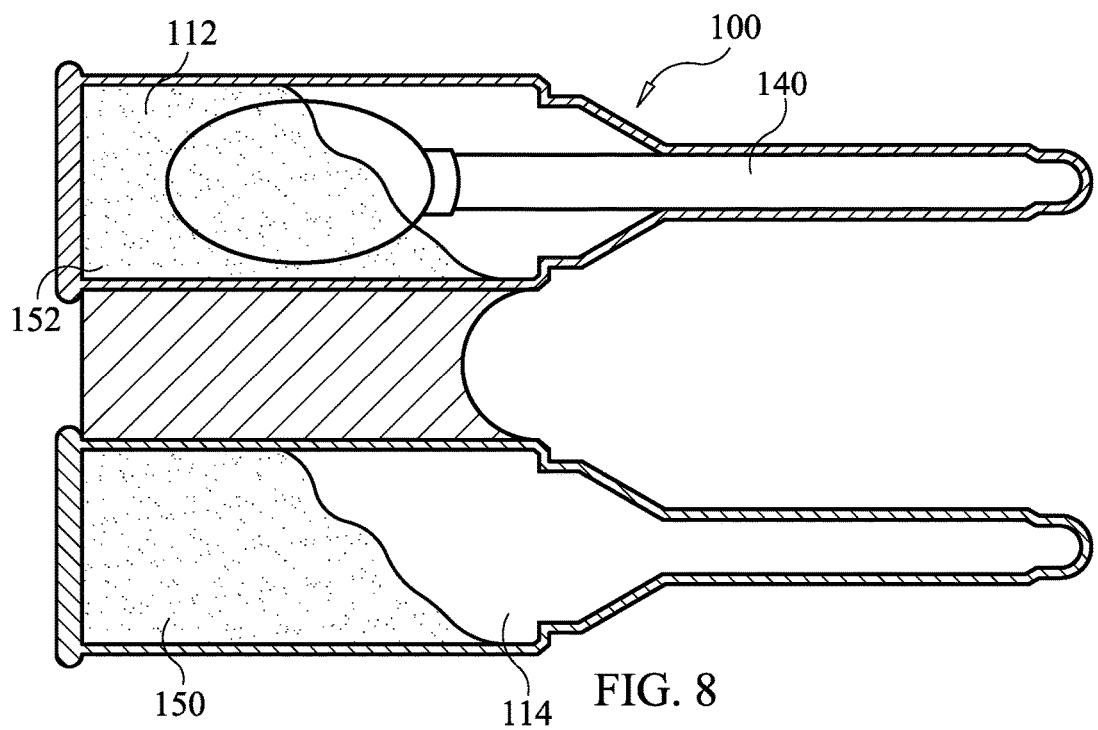
FIG. 8 illustrates a cross-sectional view of a multi-chamber container apparatus having a swab and a first solution in a first chamber and a second solution in a second chamber.
Figure 9A:
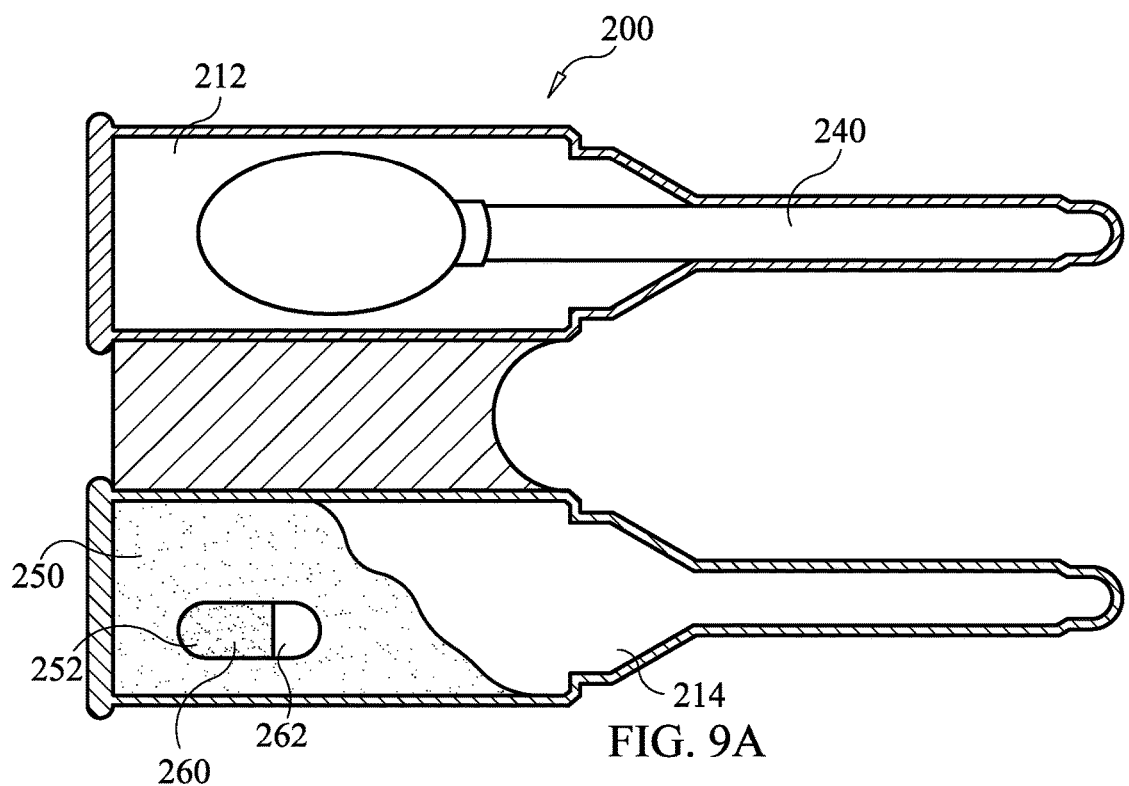
FIGS. 9A-9B illustrates cross-sectional views of a multi-chamber container apparatus having a first solution in a second chamber and a second solution in a breakable ampoule within the second chamber in an embodiment of the present invention.
Figure 9B:
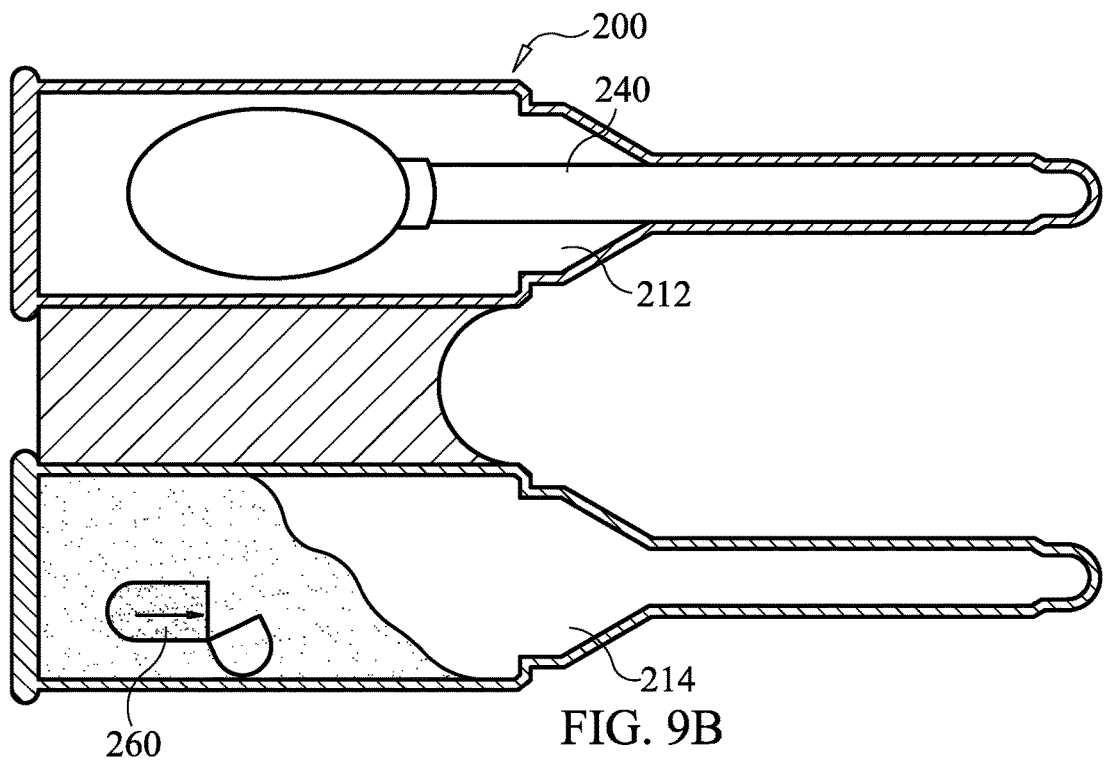

FIGS. 8 and 9A-9B illustrate alternate embodiments of the present invention. Specifically, FIG. 8 illustrates an alternate embodiment of the present invention of a multi-chamber container apparatus 100 comprising a first chamber 112, a second chamber 114, a swab or applicator 140, and a first solution or powder 150 contained within the second chamber 112, in much the same manner as described above with respect to FIGS. 1-7. However, a second solution or powder 152 may be contained in the first chamber 112. Thus, the applicator 140 may be utilized to transfer an amount of the second solution or powder 152 from the first chamber 112 to the second chamber 114 for mixing with the first solution or powder 150, and the applicator 140 may then be used to apply the mixed solution or powder as necessary. Thus, this embodiment may allow the mixing of two solutions at the time needed for use. Specifically, many medicaments may require mixing prior to use, but mixing too early prior to use may decrease or eliminate the effectiveness of the mixed solution or limit the shelf-life or usable amount of time thereof. Thus, when the applicator 140 removes the second solution or powder 152 from the first chamber 112 and is inserted into the second chamber 114, the first and second solutions or powders 150, 152 may mix, and be ready for use.

FIGS. 9A-9B illustrate yet another embodiment of the present invention of a multi-chamber container apparatus 200 having a first chamber 212 and a second chamber 214, an applicator 240 and a first solution or powder 250 contained within the second chamber 214. A breakable capsule 260 may be contained within the second chamber 214, and may contain a second solution or powder 252 therein. The breakable capsule may be made from any material that may be broken, such as, preferably, glass or, most preferably, thermoplastic. A line or area of weakness 262 may be disposed within the walls of the capsule 260 so that the same may be broken, allowing the first and second solutions or powders 250, 252 to be mixed together. For example, the capsule may be squeezed by a user through the walls of the second chamber 214 and popped open, thereby exposing the second solution 252 to the first solution 250. Shaking the multi-chamber container apparatus 200 may allow the two solutions and/or powders to mix, as shown in FIG. 9B. Thus, applicator 240 may be removed from the first chamber and inserted into the second chamber after mixing of the two solutions and/or powders.

Other embodiments may include a third solution or powder contained in the first chamber, and/or a second capsule within the third solution or powder having a fourth solution, which may be utilized as described hereinabove. In addition, three or more chambers may be utilized with various solutions and/or powders, and/or capsules contained therein for mixing any number of solutions and/or powders together, and the present invention should not be limited as described herein.

Further, each of the first and second chambers may contain a swab or applicator, and each chamber may further comprise a solution or powder. Thus, each solution or powder may be withdrawn separately from each respective chamber. For example, the first chamber may comprise an antiseptic that may be withdrawn from the chamber via a first swab contained therein and used on a wound for cleaning the wound. Next, the second chamber may comprise an antibiotic that may be removed from the second chamber via a second swab contained therein and used on wound for reducing the risk of infection and/or to aid in healing. Still further, one or both of the first and second chambers may comprise solutions or powders, and may further comprise capsules or ampoules containing yet additional solutions or powders for mixing with solutions or powders contained within each respective chamber.

Figure 10:
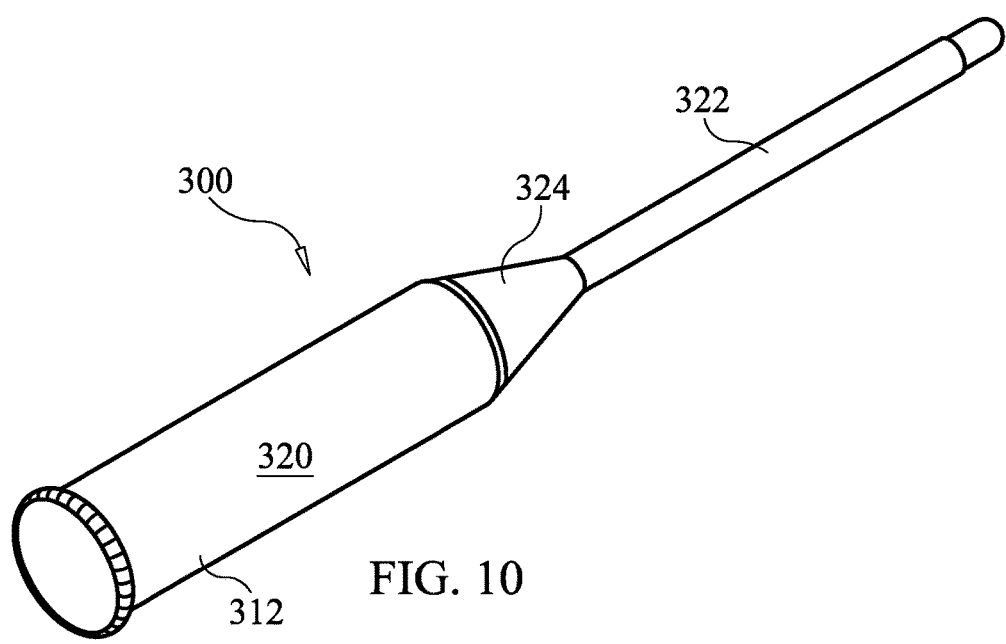
FIG. 10 illustrates a perspective view of a multi-chamber container apparatus in an alternate embodiment of the present invention.

Referring now to FIG. 10, an alternate embodiment of the present invention is provided. FIG. 10 illustrates a multi-chamber container apparatus 300 having a first chamber 312 having a main body portion 320, a stem 322 and a transitional neck portion 324. A line or area of weakness 327, as illustrated in FIGS. 11A, 11B, may be disposed within the first chamber 312 for removing the stem 322 from the main body portion 320.

Figure 11A:
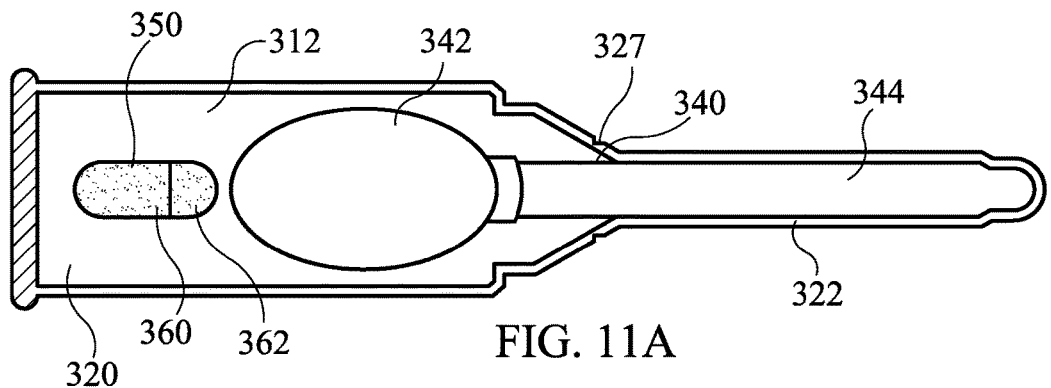
FIGS. 11A-11C illustrate cross-sectional views of a multi-chamber container apparatus having a first solution in a breakable ampoule within the container apparatus in an embodiment of the present invention.
Figure 11B:
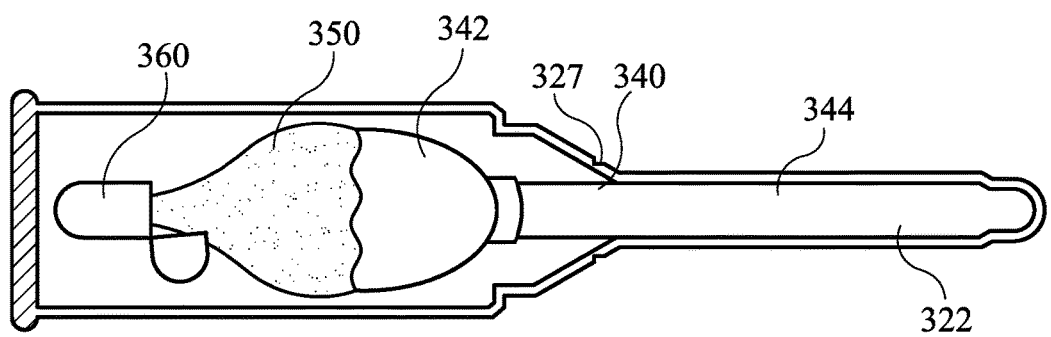
Figure 11C:
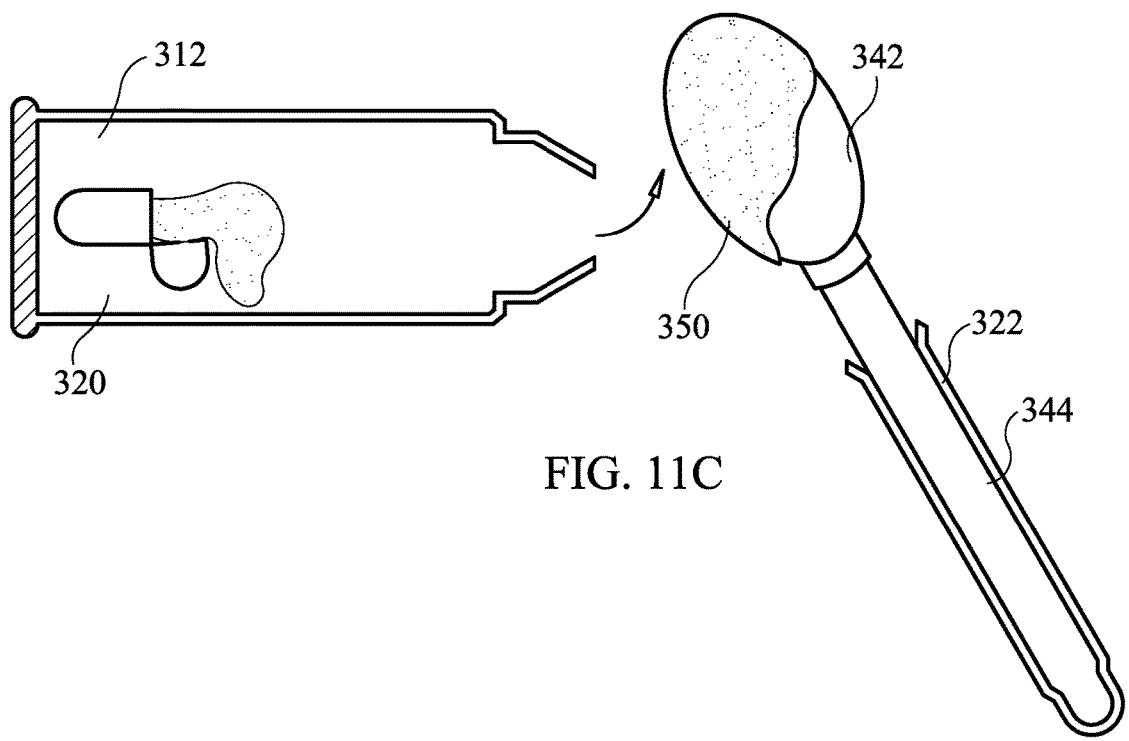

FIGS. 11A-11C illustrate cross-sectional views of the multi-chamber container apparatus 300. As shown in FIG. 11A, an applicator 340 may extend from the stem 322 having an applicator end 342 and a handle 344. An ampoule or capsule 360 forming a second chamber may be contained within the main body portion 320. The ampoule or capsule 360 may contain a first solution or powder 350 that may be released into the main body portion 320 and in contact with the applicator end 342 when the ampoule or capsule 360 is broken along a line or area of weakness 362, as illustrated in FIG. 11B. The applicator 340 may then be removed be breaking the stem 322 from the first chamber 312 via line or area of weakness 327, and the first solution or powder 350 may be utilized as needed, as illustrated in FIG. 11C. The embodiment shown in FIGS. 11A-11C may be particularly useful where the solution or powder 350 may degrade or lose effectiveness when contacting the swab or applicator 340, so the present embodiment may minimize the amount of time in contact prior to use of the solution or powder 350.

Figure 12A:
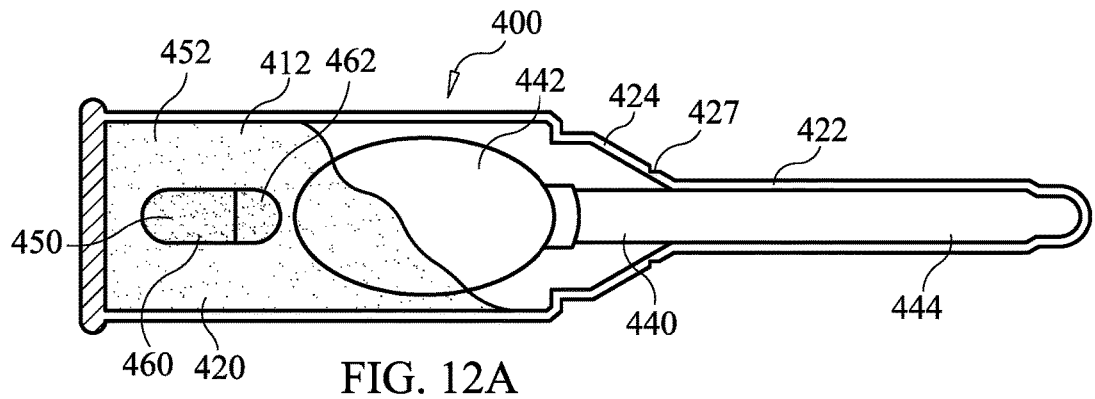
FIGS. 12A-12C illustrate cross-sectional views of a multi-chamber container apparatus having a first solution in a first chamber and a second solution within a breakable ampoule within the first chamber in an embodiment of the present invention.
Figure 12B:
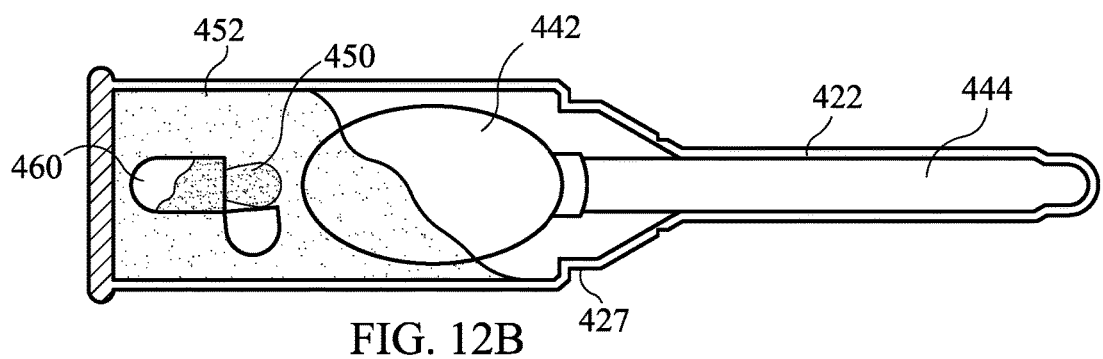
Figure 12C:
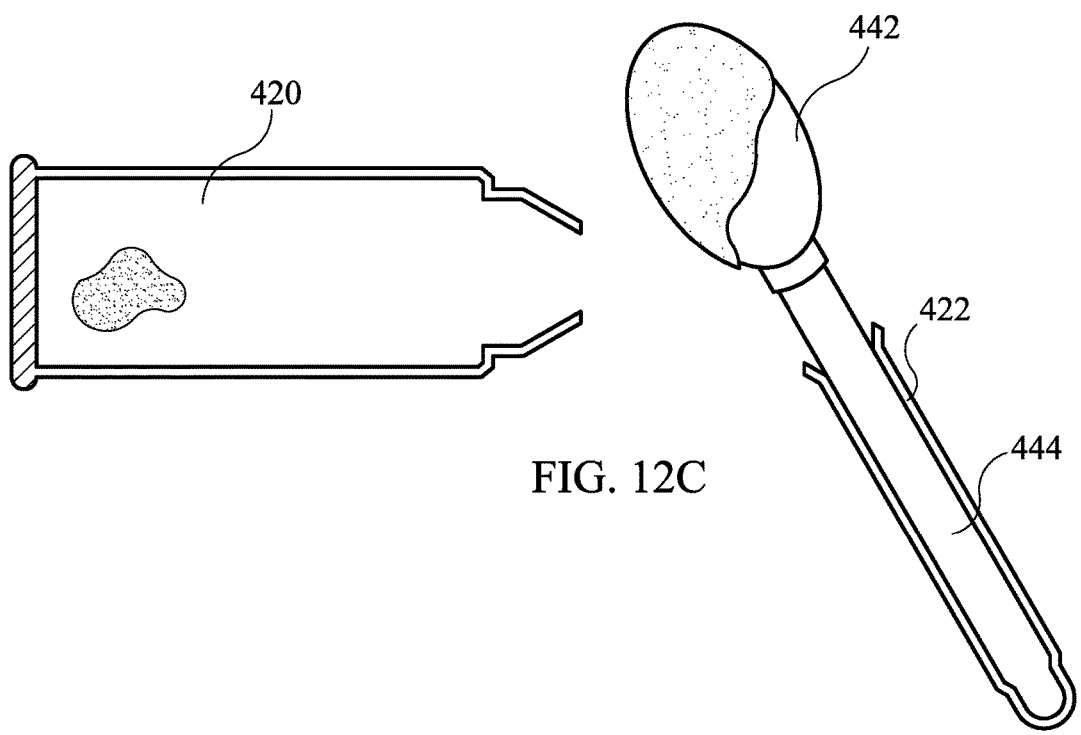

FIGS. 12A-12C illustrate cross-sectional views of a multi-chamber apparatus 400 having a first chamber 412 having a main body portion 420, a stem 422 and a transitional neck portion 424. A line or area of weakness 427 may be disposed within the first chamber 412 for removing the stem 422 from the main body portion 420.

The multi-chamber apparatus 400 may further have an applicator 440 extending from a stem having an applicator end 442 and a handle 444. An ampoule or capsule 360 forming a second chamber may be contained within the main body portion 420. The ampoule or capsule 460 may contain a first solution or powder 450 that may be released into the main body portion 420 when the capsule 460 is broken along line or area of weakness 462. A second solution or powder 452 may be contained within the main body portion 420, such that when the first solution or powder 450 is released from the ampoule or capsule 460, the first solution or powder 450 may mix with the second solution or powder 452, as illustrated in FIG. 12B. The applicator 440 may thus be removed from the first chamber 412 having a mixture of the first and second solutions and/or powders 450, 452 thereon for use as needed, as illustrated in FIG. 12C.

Figure 13A:
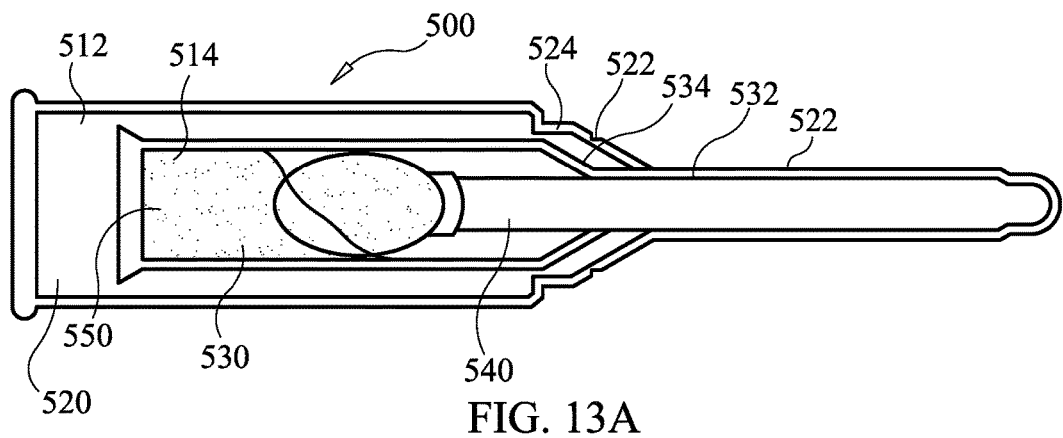
FIGS. 13A-13B illustrate cross-sectional views of a multi-chamber container apparatus having a first chamber and disposed within the first chamber is a second chamber having a swab contained therein in an embodiment of the present invention.
Figure 13B:
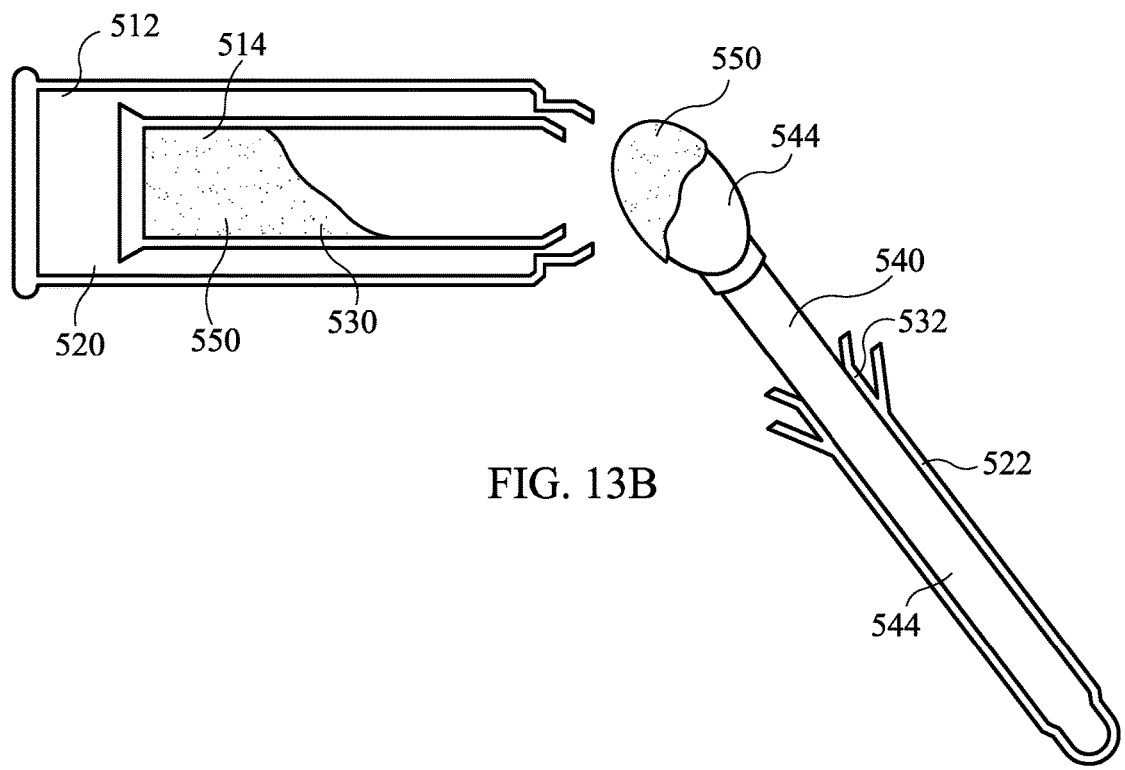

In an alternate embodiment of the present invention, illustrated in FIGS. 13A-13B, cross-sectional views of a multi-chamber container apparatus 500 is illustrated. The multi-chamber container apparatus 500 may comprise a first chamber 512 comprising a main body portion 520 a stem 522, a transitional neck portion 524 and a line or area of weakness 527. A second chamber 514 may be contained within the first chamber 512, and may comprise a main body portion 530, a stem 532, a transitional neck portion 534 and a line or area of weakness 537. A first solution 550 may be contained within the second chamber 514. Also within the second chamber may be an applicator 540 having an applicator end 542 and a handle 544 that may extend into the stem 532 of the second chamber 514 and the stem 522 of the first chamber 512.

As noted, lines or areas of weakness 427, 437 may be on both the first chamber 512 and the second chamber 514, respectively, for allowing the stems 522, 532 to be removed from the main body portions 520, 530 of the first and second chambers 512, 514, respectively. Thus, the applicator 540 may be removed from both the main body portions 520, 530 of the first and second chambers 512, 514, respectively, and the solution 550 may be utilized as needed.

This embodiment, shown in FIGS. 13A-13B, may be useful where a solution may be required to be subject to restrictions that the solution be separated in a double-walled container, or some other restriction to minimize or prevent the possibility of leakage, such as for dangerous materials, or to provide extra protection from outside materials that may degrade or destroy the solution contained therein.

In another embodiment of the present invention, the solutions or powders described herein may be colored to provide a visual indication of whether proper mixing has occurred when one or more of the solutions, powders or gels is mixed with one or more of the other solutions, powders or gels. Indeed, it is often the case that mixing one solution, powder or gel must occur prior to use thereof so that the material may have its desired effectiveness. In a first example, a multi-chamber container apparatus may comprise a first liquid, powder or gel of a first color and a second liquid, powder or gel of a second color. Upon mixing of the liquid, powder or gel, the first color may combine with the second color thereby forming a third color. A user thereof will know when proper mixing occurs when the third color is apparent. Alternatively, the first and second liquids, powders or gels may comprise first and/or second colors, or no differentiating color. Upon mixing of the first and second liquids, powders or gels, a chemical reaction may occur causing a distinctive coloring of the mixture thereof, visually indicating to a user that proper mixing has occurred.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

We claim:

1. A multi-chamber container apparatus comprising:
   a first chamber having a main body portion and an extended portion, the first chamber having a wall and an area of weakness within the wall for separating the main body portion and the extended portion from each other when the first chamber is broken at the area of weakness, and an applicator disposed within the first chamber having a handle and an applicator end, the handle of the applicator extending from the extended portion such that the applicator end is disposed within the main body portion;
   a second chamber having a main body portion and an extended portion, the second chamber having a wall and an area of weakness within the wall for separating the main body portion and the extended portion of the second chamber from each other when the second chamber is broken at the area of weakness, and a first material within the second chamber for application to the applicator end when the applicator end is inserted into the second chamber,
   wherein the first and second chambers are connected to each other in a side-by-side configuration.

2. The multi-chamber container apparatus of claim 1 wherein the applicator end is a swab.

3. The multi-chamber container apparatus of claim 1 wherein the first material is selected from the group consisting of a liquid, a powder and a gel.

4. The multi-chamber container apparatus of claim 1 further comprising:
   a fin disposed between the first and second chambers for separating the first and second chambers from each other.

5. The multi-chamber container apparatus of claim 1 wherein the wall of the first chamber and the wall of the second chamber are interconnected together.

6. The multi-chamber container apparatus of claim 1 further comprising:
   a transitional neck between the main body portion and the extended portion of the first chamber.

7. The multi-chamber container apparatus of claim 6 wherein the area of weakness is disposed on the transitional neck.

8. The multi-chamber container apparatus of claim 1 further comprising:
   a second material contained within the second chamber, wherein the second material is selected from the group consisting of a liquid, a powder and a gel.

9. The multi-chamber container apparatus of claim 1 further comprising:
   a capsule within the first or second chambers, wherein the capsule comprises an area of weakness for opening the capsule, the capsule further comprising a second material wherein the second material is selected from the group consisting of a liquid, a powder and a gel.

10. The multi-chamber container apparatus of claim 9 wherein the capsule is in the second chamber, such that breaking the capsule at the area of weakness causes the first and second materials to mix.

11. A method of using a multi-chamber container apparatus comprising the steps of:
    providing a multi-chamber container apparatus comprising a first chamber having a main body portion and an extended portion, the first chamber having a wall and an area of weakness within the wall for separating the main body portion and the extended portion from each other when the first chamber is broken at the area of weakness, and an applicator disposed within the first chamber having a handle and an applicator end, the handle of the applicator extending from the extended portion such that the applicator end is disposed within the main body portion; a second chamber having a main body portion and an extended portion, the second chamber having a wall and an area of weakness within the wall for separating the main body portion and the extended portion of the second chamber from each other when the second chamber is broken at the area of weakness, and a first material within the second chamber for application to the applicator end when the applicator end is inserted into the second chamber, wherein the first and second chambers are connected to each other in a side-by-side configuration;

breaking the first chamber at the area of weakness on the first chamber;

breaking the second chamber at the area of weakness on the second chamber;

withdrawing the applicator from the first chamber; and inserting the applicator into the second chamber and applying the first material to the applicator.

12. The method of claim 11 wherein the applicator end is a swab, and the first material is absorbed by the swab when inserted into the second chamber.

13. The method of claim 11 wherein the second chamber comprises a second material and further comprising the step of:
   mixing the first and second materials together when the applicator is inserted into the second chamber.

14. The multi-chamber container of claim 11 wherein the first or second chambers comprise a capsule within the first or second chambers, wherein the capsule comprises an area of weakness for opening the capsule, the capsule further comprising a second material, and further comprising the step of:
   breaking the capsule at the area of weakness and releasing the second material into the first or second chamber.

15. The multi-chamber container apparatus of claim 14 wherein the capsule is in the second chamber, such that breaking the capsule at the area of weakness causes the first and second materials to mix to form a mixture, and further comprising the step of:
   applying the mixture to the applicator when the applicator is inserted into the second chamber.

\* \* \* \* \*